US008349370B2

(12) United States Patent
Kobayashi et al.

(10) Patent No.: US 8,349,370 B2

(45) Date of Patent: Jan. 8, 2013

(54) BLOAT CONTROLLING AGENT FOR A RUMINANT

(75) Inventors: Yasuo Kobayashi, Sapporo (JP); Kyo Nagashima, Sodegaura (JP); Masami Mochizuki, Sodegaura (JP)

(73) Assignee: National University Corporation Hokkaido University, Sapporo-shi (JP)

( * ) Notice: Subject to any disclaimer, the term of this patent is extended or adjusted under 35 U.S.C. 154(b) by 11 days.

(21) Appl. No.: 12/663,598

(22) PCT Filed: Jun. 6, 2008

(86) PCT No.: PCT/JP2008/060492

§ 371 (c)(1), (2), (4) Date: Dec. 8, 2009

(87) PCT Pub. No.: WO2008/149994

PCT Pub. Date: Dec. 11, 2008

(65) Prior Publication Data

US 2010/0183755 A1 Jul. 22, 2010

(30) Foreign Application Priority Data

Jun. 8, 2007 (JP) ................................. 2007-153285
Feb. 8, 2008 (JP) ................................. 2008-029494

(51) Int. Cl.
*A61K 36/00* (2006.01)
*A61K 36/87* (2006.01)

(52) U.S. Cl. ....................................... 424/725; 424/776

(58) Field of Classification Search ........................ None
See application file for complete search history.

(56) References Cited

U.S. PATENT DOCUMENTS

| | | | | |
|---|---|---|---|---|
| 5,725,894 | A | 3/1998 | Toyomizu et al. | |
| 6,379,694 | B1 * | 4/2002 | Hatano et al. | 424/442 |
| 2008/0008774 | A1 | 1/2008 | Becker et al. | |

FOREIGN PATENT DOCUMENTS

| | | |
|---|---|---|
| JP | 3 217484 | 9/1991 |
| JP | 8 231410 | 9/1996 |
| WO | WO 2005/099729 A2 | 10/2005 |

OTHER PUBLICATIONS

McGuffey et al, Ionophores for dairy cattle: current status and future outlook, Journal of Dairy Science (2001) vol. 84, Number Elect. Supplement, pp. E194-E203.*
Nagabhushana et al, Selective ionophoric properties of anacardic acid, Journal of Natural Products, 1995, 58 (5): 807-810.*
Cheng K.J. et al., "A review of bloat in feedlot cattle", Journal of Animal Science, vol. 76, Issue 1, pp. 299-308, (1998).
Himejima Masaki et al., "Antibacterial Agents from the Cashew Anacardium occidentale (Anacardiaceae) Nut Shell Oil", Journal of Agricultural and Food Chemistry, vol. 39, No. 2, pp. 418-421, (1991).
U.S. Appl. No. 12/663,607, filed Dec. 8, 2009, Kobayashi, et al.
Extended European Search Report issued Feb. 18, 2011, in European Application No. 08777112.7.
C. J. Van Nevel, et al., "Effect of Fatty Acid Derivatives on Rumen Methane and Propionate In Vitro", Applied Microbiology, vol. 21, No. 2, XP002617171, Feb. 1971, pp. 365-366.
Isao Kubo, et al., "Structure-Antibacterial Activity Relationships of Anacardic Acids", Journal of Agricultural & Food Chemistry, vol. 41, No. 6, XP000369580, pp. 1016-1019, 1993.
T. G. Nagaraja, et al., "Ruminal Acidosis in Beef Cattle: The Current Microbiological and Nutritional Outlook", Journal of Dairy Science, American Dairy Science Association, vol. 90, XP026956032, Jun. 1, 2007, pp. E17-E38.
O. Sreemannarayana, et al., "A note on the production volatile fatty acids by bovine rumen liquor in artificial rumen in the presence of cashew apple and water-hyacinth meals", Indian Journal of Animal Sciences, vol. 43, No. 6, XP009143301, pp. 545-546, 1972.
Y. Watanabe, et al., "In vitro evaluation of cashew nut shell liquid as a methane-inhibiting and propionate-enhancing agent for ruminants", Journal of Dairy Science, vol. 93., No. 11, XP009143295, Nov. 2010, pp. 5258-5267.
U.S. Appl. No. 13/139,127, filed Jun. 10, 2011, Nagashima, et al.

* cited by examiner

*Primary Examiner* — Qiuwen Mi
(74) *Attorney, Agent, or Firm* — Oblon, Spivak, McClelland, Maier & Neustadt, L.L.P.

(57) ABSTRACT

The present invention provides a bloat controlling agent for a ruminant, comprising cashew nut shell liquid.

8 Claims, No Drawings

BLOAT CONTROLLING AGENT FOR A RUMINANT

This application is a 371 of PCT/JP08/60492, filed Jun. 6, 2008.

TECHNICAL FIELD

The present invention relates to a bloat controlling agent including cashew nut shell liquid.

BACKGROUND ART

Infectious diseases of a domestic animal cause a weight decrease of the domestic animal and induce various pathologies, and hence remarkably lower the commercial value of the domestic animal. For example, *Staphylococcus aureus* is a bacterium causing mastitis, subcutaneous tumor, and pyemia of bovines, sheep, and goats, anthema of horses, and arthritis, dermatitis, and ichorrhemia of pigs and chickens. Further, *Streptococcus suis* is a bacterium causing meningitis, ichorrhemia, endocarditis, and arthritis of pigs, and *Streptococcus bovis* is a bacterium causing a bloat of bovines.

The bloat refers to the following state: rumen juice is formed into a foamed state so that gas is not separated from liquid, and the accumulated gas cannot be expelled by eructation. The gas compresses the heart and the lungs, and the animal dies when they are left as it is. When the animal is fed with a feed containing a small amount of coarse feed and a large amount of starch such as corn, *Streptococcus bovis* increases in the rumen, and the rumen juice is formed into a foamed state due to the generated viscous substance.

It is known that cashew nut shell liquid has an antibacterial action (Non-patent Document 1) and a coccidiosis-relieving action (Patent Document 1).

Further, it is reported that the cashew nut shell liquid has antibacterial action against Gram-positive bacteria such as *Staphylococcus aureus, Streptococcus mutans, Bacillus subtilis*, and *Bacillus ammoniagenes*, and does not have antimicrobial action against Gram-negative bacteria such as *Escherichia coli, Enterobacter aerogenes*, and *Pseudomonas aeruginosa*, and against fungi such as *Saccharomyces cerevisiae, Candida Utilis*, and *Penichillium chrysogenum* (Non-patent Document 2). However, the antibacterial action of the cashew nut shell liquid against *S. bovis* is not known, and there is no report at all on the preventive effect against a bloat.

Patent Document 1: JP 08-231410 A

Non-patent Document 1: Muroi, H. et al., Bioorganic & Medicinal Chemistry 12, 583-587 (2004)

Non-patent Document 2: Himejima M. and Kubo I., J. Agric. Food Chem., 39, 418-421 (1991)

DISCLOSURE OF THE INVENTION

An object of the present invention is to suppress a bloat of a ruminant.

The inventors of the present invention have conducted intensive studies in order to solve the above problem, and as a result, the inventors have found that cashew nut shell liquid can be used for the control of a bloat. Thus, the inventors of the present invention have completed the present invention.

That is, the present invention is as follows:

(1) A bloat controlling agent for a ruminant, comprising cashew nut shell liquid.

(2) A bloat controlling agent according to (1), wherein the bloat is caused by *Streptococcus bovis*.

(3) A composition for a feed for controlling a bloat, comprising the bloat controlling agent according to (1) or (2).

(4) A feed for controlling a bloat, comprising the composition for a feed according to (3).

(5) A composition for a feed for controlling a bloat, comprising cashew nut shell liquid.

(6) A feed for controlling a bloat, comprising cashew nut shell liquid.

(7) A method of controlling a bloat of a ruminant, comprising administering cashew nut shell liquid to a ruminant.

(8) Use of cashew nut shell liquid in manufacturing a bloat controlling agent for a ruminant.

(9) Use of cashew nut shell liquid in manufacturing a composition for a feed for controlling a bloat.

(10) Use of cashew nut shell liquid in manufacturing a feed for controlling a bloat.

The bloat controlling agent of the present invention can be used for controlling a bloat of a ruminant.

BEST MODE FOR CARRYING OUT THE INVENTION

A bloat controlling agent for a ruminant of the present invention includes cashew nut shell liquid (CNSL).

The cashew nut shell liquid to be used in the present invention is an oily liquid contained in the shell of the seed of a cashew nut tree (*Anacardium occidentale L.*). The cashew nut shell liquid contains, as the components thereof, anacardic acids, cardanol, and cardol.

The cashew nut shell liquid used in the present invention can be obtained as a vegetable oil extracted by compressing the shell of a cashew nut. Further, the cashew nut shell liquid used in the present invention can also be obtained by heating or extracting, e.g., dry-distilling or solvent-extracting a cashew nut shell. In addition, the cashew nut shell liquid used in the present invention can be obtained according to a method described in JP 08-231410 A.

The cashew nut shell liquid used in the present invention may also be a heat-sterilized oil and a liquid obtained by pulverizing/crushing the shell of a cashew nut.

For the cashew nut shell liquid used in the present invention, a commercially-available product may also be used.

The content of the cashew nut shell liquid in the bloat controlling agent of the present invention is, from the view points of effects and costs, preferably 10 mass % to 100 mass %, more preferably 5 mass % to 90 mass %, and still more preferably 10 mass % to 80 mass %, with respect to a total amount of the controlling agent. When the content is 1 mass % or more, the bloat controlling effect can be exhibited with a predetermined amount of the controlling agent. Further, a stock solution of cashew nut shell liquid may be directly orally administered. In addition, in the present invention, control includes both prevention and therapy.

Further, because the cashew nut shell liquid exhibits antibacterial action against *Streptococcus bovis*, the bloat controlling agent of the present invention can be used to control the bloat caused by *Streptococcus bovis*.

The bloat in the present invention includes a bloat caused by leguminous pasture or concentrated feed, and the bloat controlling agent of the present invention also has an effect on such a bloat.

The bloat controlling agent of the present invention may further contain, in addition to the cashew nut shell liquid, an arbitrary component(s) such as a component which is effective for the growth promotion of a ruminant, a nutritional supplement component, a component for enhancing the preservation stability. Examples of the arbitrary components include the followings: probiotics such as *Enterococcus, Bacillus*, and *Bifidus;* enzymes such as amylase and lipase; vitamins such as L-ascorbic acid, choline chloride, inositol, and folate; minerals such as potassium chloride, iron citrate, magnesium oxide, and phosphates; amino acids such as DL-alanine, DL-methionine, L-lysine; organic acids such as fumaric acid, butyric acid, lactic acid, acetic acid, and their salts; antioxidants such as ethoxyquin, dibutylhydroxytoluene, butylhydroxy anisole, ferulic acid, vitamine C, and vitamine E; fungicides such as calcium propionate; binders such as carboxylmethyl cellurose (CMC), casein sodium, and sodium polyacrylate; emulsifiers such as lecithin, glycerin fatty acid ester and sorbitan fatty acid ester; pigments such as astaxanthin and canthaxanthin; and flavoring agents such as various esters, ethers, and ketones.

The formulation of the bloat controlling agent of the present invention is not particularly limited, and the agent may be in an arbitrary form such as powder, liquid, solid, a tablet, a capsule, or emulsion. The bloat controlling agent of the present invention can be produced by mixing cashew nut shell liquid and, if required, an arbitrary component, and forming the mixture into a preparation. Note that, depending on the form of the formulation, the pulverized/crushed product of the above-mentioned cashew nut shell or the cashew nut shell as it is without being subjected to any treatment is mixed with another arbitrary component, and the mixture can be used as the bloat controlling agent of the present invention. In addition, without being mixed with another arbitrary component, the pulverized/crushed product as it is or the cashew nut shell as it is may be used as the bloat controlling agent, and the bloat controlling agent itself may be used as a composition for a feed or a feed.

The composition for a feed of the present invention includes cashew nut shell liquid. Further, the composition for a feed of the present invention may also include the bloat controlling agent. The content of the cashew nut shell liquid in the composition for a feed of the present invention is, from the viewpoints of effects and costs, preferably 0.5 to 500,000 mass ppm, more preferably 5 to 100,000 mass ppm, and still more preferably 50 to 50,000 mass ppm with respect to a dry mass of the composition for a feed.

In the case of using the bloat controlling agent of the present invention as the composition for a feed, the bloat controlling agent is mixed with another feed component used in pet foods and supplements for pets (hereinafter referred to as feed), to thereby produce a feed. The kind of the feed and the components other than the cashew nut shell liquid are not particularly limited.

The feed of the present invention includes cashew nut shell liquid. In addition, the feed may also include the above-mentioned composition for a feed.

Note that the content of the cashew nut shell liquid in the feed of the present invention is, in terms of effect and cost, preferably 0.5 to 50,000 mass ppm, more preferably 5 to 10,000 mass ppm, and still more preferably 50 to 5,000 mass ppm with respect to a dry mass of the feed.

The feed of the present invention can be produced by adding cashew nut shell liquid or a composition for a feed including the cashew nut shell liquid as it is to a feed component and mixing the resultant. On this occasion, when a powdery or solid composition for a feed is used, the form of the composition for a feed may be modified into a liquid form or a gel form for the purpose of facilitating the mixing process. In this case, the following may be used as a liquid carrier: water; a vegetable oil such as soybean oil, rapeseed oil, or corn oil; or a water-soluble polymer compound such as a liquid animal oil, polyvinylalcohol, polyvinylpyrrolidone, or polyacrylic acid. Further, in order to keep the uniformity of the cashew nut shell liquid in the feed, the feed also preferably contains alginic acid, sodium alginate, xanthan gum, casein sodium, gum arabic, guar gum, or water-soluble polysaccharides such as tamarind seed polysaccharide.

The species of animals that ingest the feed of the present invention is preferably ruminants. The feed of the present invention is suitable for breeding, for example, ruminants such as cows, goats, and sheep. The amount of feed ingested by an animal may be appropriately adjusted depending on the animal's species, body weight, age, sex, health condition, feed component, etc. In this case, the amount of cashew nut shell liquid contained in the feed is preferably 0.005 to 500 g per ruminant per day, more preferably 0.5 to 100 g per ruminant per day, and still more preferably 0.5 to 50 g per ruminant per day.

Any method usually used may be adopted as a method of feeding animals and a method of breeding animals depending on the species of animals.

EXAMPLES

Example 1

Antibacterial Action of CNSL against *S. bovis*

Cashew nut shell liquid (CNSL) extracted by compressing a cashew nut shell was obtained from Cashew Trading Co., Ltd.

For examining the antibacterial action of CNSL, the following strains were each cultured in a brain-heart-infusion medium (manufactured by NISSUI PHARMACEUTICAL CO., LTD.) at 37° C. for a day: *Staphylococcus aureus* strain isolated from a bovine; *S. bovis* DSM20065 strain; *Bacillus subtilis* NBRC3009 strain; *Escherichia coli* ATCC11303 strain; *Pseudomonas aeruginosa* NBRC12689 strain; and *Saccharomyces cerevisiae* NBRC10217 strain. Into the brain-heart-infusion medium to which CNSL was added, 10 μL of each culture media of the above-mentioned strains was inoculated, and the resultant was cultured at 37° C. for two days, to thereby calculate a minimum growth-inhibitory concentration (MIC).

Table 1 shows the results.

TABLE 1

| | | MIC (μg/ml) |
|---|---|---|
| Gram-positive bacteria | *Staphylococcus aureus* isolated from a bovine | 6.25 |
| | *Streptococcus bovis* DSM20065 | 9.38 |
| | *Bacillus subtilis* NBRC3009 | 6.25 |
| Gram-negative bacteria | *Escherichia coli* ATCC11303 | >1,600 |
| | *Pseudomonas aeruginosa* NBRC12689 | >1,600 |
| Fungus | *Saccharomyces cerevisiae* NBRC10217 | >1,600 |

CNSL also has high antibacterial action against *S. bovis* in the same manner as against *Staphylococcus aureus* and *Bacillus subtilis*, which are Gram-positive bacteria. *S. bovis* is a bacterium which is present in the rumen and is considered as one of the bacteria causing a bloat. Therefore, it is thought that, as one of the working mechanisms of the bloat controlling agent of the present invention, the proliferation of *S. bovis* can be suppressed in the rumen by administering CNSL, thereby being capable of preventing a bloat.

Example 2

Effects with Time of CNSL Administration In Vivo (1) Sample

Four sheep fitted with rumen cannula were each provided with a feed (concentrated feed: hay=3:7 (volume)) in an amount equivalent to 1.4 mass % of the weight of the each sheep.

A first sampling of rumen contents was performed before starting the administration of CNSL. As for the dose of CNSL, rumen function-improving effects were observed with the addition of 100 mg/L or more of CNSL in the test in vitro. In order to allow the concentration of CNSL in the rumen juice of the sheep to be 100 mg/L, it is required to mix 0.14 to 0.28 mass % (1,400 to 2,800 mass ppm) of CNSL into the feed, because CNSL is diluted in the rumen juice. Accordingly, 0.14 mass % of CNSL was added to the feed for the first two weeks and the sampling of rumen contents was performed once a week, i.e., twice in total. 0.28 mass % of CNSL was added to the feed for the next two weeks and the sampling of rumen contents was performed once a week, i.e., twice in total. For the next two weeks, only a feed in which CNSL is not added was provided to the sheep, and the sampling of rumen contents was performed once a week, i.e., twice in total.

(2) Results

Table 2 shows the pH of the rumen juice.

TABLE 2

| | CNSL dose | pH |
|---|---|---|
| Before starting administration | — | 7.11 ± 0.08 |
| First week | 0.14 mass % | 6.78 ± 0.28* |
| Second week | 0.14 mass % | 7.03 ± 0.15 |
| Third week | 0.28 mass % | 6.98 ± 0.11 |
| Fourth week | 0.28 mass % | 7.05 ± 0.06 |
| Fifth week | Discontinuation of administration | 6.86 ± 0.10** |
| Sixth week | Discontinuation of administration | 6.76 ± 0.20** |

*P < 0.10 compared to before starting administration
**P < 0.05 compared to before starting administration The pH of the rumen juice lowered when the administration of CNSL was stopped. Consequently, it is found that CNSL has an effect of preventing pH decline of the rumen juice. That is, it is found that CNSL has an effect of controlling rumen acidosis which causes rumen juice to be oxidized and deteriorates the rumen function.

Table 3 shows the viscosity of the rumen juice (CP), the foamability of the rumen juice (IVI (%)), and the foam stability of the rumen juice (sIVI (%)).

TABLE 3

| | CNSL dose | CP | IVI (%) | sIVI (%) |
|---|---|---|---|---|
| Before starting administration | — | 4.51 ± 0.60 | 7.67 ± 1.15 | 6.33 ± 1.28 |
| First week | 0.14 mass % | 3.63 ± 1.15 | 6.67 ± 1.63 | 5.83 ± 1.67 |
| Second week | 0.14 mass % | 2.77 ± 1.05** | 3.50 ± 1.14** | 2.83 ± 1.00** |
| Third week | 0.28 mass % | 2.40 ± 0.49** | 1.67 ± 1.15** | 1.33 ± 0.44** |
| Fourth week | 0.28 mass % | 2.84 ± 0.36** | 1.83 ± 0.33** | 1.17 ± 1.00** |
| Fifth week | Discontinuation of administration | 2.81 ± 0.67** | 6.17 ± 3.98 | 4.50 ± 3.53 |
| Sixth week | Discontinuation of administration | 3.64 ± 1.55 | 6.83 ± 4.47 | 5.00 ± 2.91 |

*P < 0.10 compared to before starting administration
**P < 0.05 compared to before starting administration Bovine bloat is such a disease that rumen juice is formed into a foamed state and the bovine becomes unable to expel gas by eructation, so the gas is accumulated in the rumen and causes bloating in the abdomen. When the symptom becomes severe, the gas compresses the heart and the lungs, leading to death. The viscosity, foamability, and foam stability of the rumen juice each lowered by the administration of CNSL, and each increased when the administration was stopped. That is, it is found that CNSL has an effect of controlling the bloat.

Industrial Applicability

When a ruminant is raised by allowing them to ingest cashew nut shell liquid, a bloat can be controlled.

The invention claimed is:

1. A method for controlling bloating or acidosis in a ruminant comprising administering to a ruminant in need thereof an amount of a composition comprising cashew nut shell liquid sufficient to suppress bloating or to reduce acidosis.

2. The method of claim 1, wherein said ruminant has bloating, comprising administering to a ruminant in need thereof an amount of cashew nut shell liquid sufficient to suppress bloating.

3. The method of claim 1, wherein said ruminant has acidosis, comprising administering to a ruminant in need thereof an amount of cashew nut shell liquid sufficient to reduce acidosis.

4. The method of claim 1, comprising administering 0.005 to 500 g of said composition per day to the ruminant.

5. The method of claim 4, wherein said bloating is caused by *Streptococcus bovis*.

6. The method of claim 1, wherein the cashew nut shell liquid comprises anacardic acid, cardanol and cardol.

7. The method of claim 2, comprising administering 0.005 to 500 g of said composition per day to the ruminant.

8. The method of claim 3, comprising administering 0.005 to 500 g of said composition per day to the ruminant.

* * * * *

UNITED STATES PATENT AND TRADEMARK OFFICE
CERTIFICATE OF CORRECTION

PATENT NO. : 8,349,370 B2
APPLICATION NO. : 12/663598
DATED : January 8, 2013
INVENTOR(S) : Yasuo Kobayashi et al.

It is certified that error appears in the above-identified patent and that said Letters Patent is hereby corrected as shown below:

On the title page, Item (73), the Assignee's information is incorrect. Item (73) should read as follows:

--(73) Assignees: Idemitsu Kosan Co., Ltd., Tokyo, (JP);
National University Corporation Hokkaido University,
Sapporo-shi, (JP)--

Signed and Sealed this
Sixth Day of August, 2013

Teresa Stanek Rea
*Acting Director of the United States Patent and Trademark Office*